United States Patent
Sanchez

(10) Patent No.: US 6,507,954 B1
(45) Date of Patent: Jan. 21, 2003

(54) MECHANICAL VISUAL PROTECTOR FOR WELDING APPLICATION

(76) Inventor: John Alejandro Sanchez, Calle 8# 26-64 Capital District, Bogota (CO)

( * ) Notice: Subject to any disclaimer, the term of this patent is extended or adjusted under 35 U.S.C. 154(b) by 0 days.

(21) Appl. No.: 09/633,135

(22) Filed: Aug. 4, 2000

(30) Foreign Application Priority Data

Aug. 6, 1999 (CO) .......................................... 99-049821

(51) Int. Cl.⁷ .................................................. A61F 9/00
(52) U.S. Cl. ...................................................... 2/15; 2/8
(58) Field of Search ........................... 2/15, 8, 427, 431, 2/432

(56) References Cited

U.S. PATENT DOCUMENTS

| | | | | |
|---|---|---|---|---|
| 2,086,208 A | * | 7/1937 | Brekelbaum | |
| 2,154,774 A | * | 4/1939 | Rienacker et al. | |
| 2,582,860 A | * | 1/1952 | Clerke | |
| 2,693,597 A | * | 11/1954 | Horlbeck | |
| 2,761,046 A | * | 8/1956 | Herrick et al. | |
| 3,096,430 A | * | 7/1963 | Farr | |
| 3,327,317 A | * | 6/1967 | Vattuone | |
| 3,368,220 A | * | 2/1968 | Wenzel | |
| 3,838,247 A | * | 9/1974 | Finger et al. | |
| 4,011,594 A | * | 3/1977 | Guilbaud et al. | |
| 4,101,979 A | * | 7/1978 | Tarrone | 2/8 |
| 4,109,132 A | * | 8/1978 | Butoi | 2/8 |
| 4,571,741 A | * | 2/1986 | Guillaumot | 2/8 |
| 4,679,255 A | * | 7/1987 | Kuhlman | 2/8 |
| 4,694,141 A | * | 9/1987 | Hahn | 2/8 |
| 4,937,879 A | * | 7/1990 | Hall et al. | 2/8 |
| 6,008,466 A | * | 12/1999 | Hosoda | 2/8 X |

FOREIGN PATENT DOCUMENTS

| | | | | |
|---|---|---|---|---|
| DE | 2737836 | * | 3/1979 | 2/8 |
| FR | 1288008 | * | 2/1962 | 2/8 |
| GB | 456424 | * | 11/1936 | 2/8 |
| SE | 100611 | * | 1/1941 | 2/8 |

* cited by examiner

*Primary Examiner*—Rodney M. Lindsey
(74) *Attorney, Agent, or Firm*—Kramer & Assc. P.C.

(57) ABSTRACT

The present invention is a device and apparatus to protect a welder's eyesight, including a protective shield in a window frame, the frame having a pivotable slotted flange acting as a socket for a rotatable wire rope anchor connected, through the flange, by a wire rope to an automatic or manual, remotely operable actuator. The actuator can be conveniently mounted to welding equipment, such as a cutting handle, using an interchangeable base. The base has means for attachment to the cutting handle, and means for removable and/or adjustable attachment to the actuator device using interlocking mounts. The invention further includes a means to inhibit energy flow to welding equipment while the vision-protecting window is open.

19 Claims, 10 Drawing Sheets

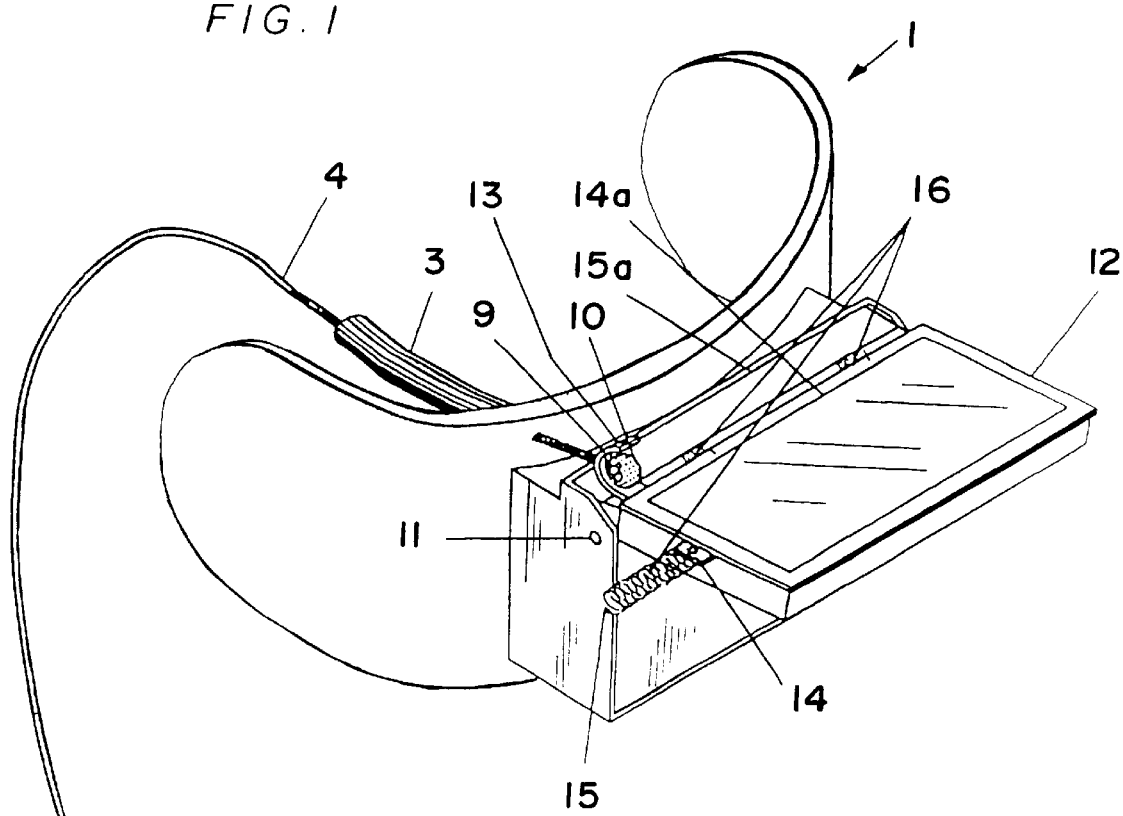
FIG. 1
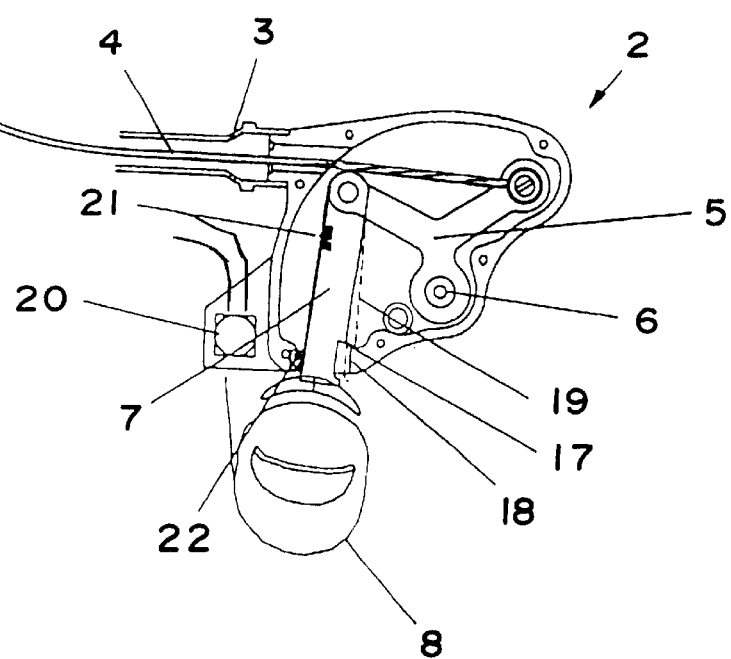

MECHANICAL VISUAL PROTECTOR FOR WELDING APPLICATION

CROSS-REFERENCE TO RELATED APPLICATIONS

This application claims priority to co-pending Colombian Patent Application No. 9949821.

BACKGROUND OF THE INVENTION

1. Field of the Invention

The present invention relates to welding shields and, more particularly, welding shields having manual or automatic, remotely operable vision protecting windows.

2. Description of the Prior Art

When performing welding, a face shield is used in which a filter-holder window (or window frame) is manually operated, typically requiring the use of at least one arm to raise and to lower the shield. When pointing to the welding target, it is relatively troublesome to lower and to lift up the vision protector at each welding point. Thus, a disproportionate effort may be required when welding, due to repeated lowering and raising of the face shield. For this reason, many welders choose to refrain from using the face shield, considering that it will often suffice to ignore the safety device and simply turn the face to keep from being injured by the rays coming from weld light. However, the result of taking this approach can be accidental direct visual exposure to welding light.

It is also laborious to handle the face shield when one's hands are in use, e.g., when applying welding material such as inox. steel (Argon). When welding material is applied, often the welding point is located, and the vision protector is operated, by the same arm. This can lead to improper targeting of the welding site by the welding tool, and occasional application of the welding tool upon a site other than what is required or intended.

Some prior art face shields include a vision protector comprising a lens which darkens with welding light contact. Despite the relatively fast darkening of such lenses, due to the velocity of the welding light, the rate at which the lens darkens will never be greater than or even equal to the rate at which the welding light rays can travel from the point of welding application to the shield lens or eye.

SUMMARY OF THE INVENTION

The present invention addresses the inconvenience referred to above by outfitting the vision protecting window of welding equipment with a remotely operable (foot or finger actuated) actuator, powered by lever with rope wire, or with hydraulic, pneumatic, solar or electric power to conveniently and easily open and shut the window. The device also reduces the number of accidents involving direct eye exposure to welding light by including a means to inhibit the energy flow to the handle or cutter portion of welding equipment while the eye protecting window is open, and to automatically resume energy flow when the window is closed or shut.

Accordingly, it is a principle object of the invention to ensure that the protective window is closed during the welding process.

It is another object of the invention to enable the window mechanisms to be opened and closed as many times as required while welding is performed in a safe and efficient manner, thus maintaining welding application effectiveness and work quality.

To further elucidate the invention, its features and advantages are described in detail, and supported by the following drawings:

BRIEF DESCRIPTION OF THE DRAWINGS

FIG. 1 is a perspective and schematic view of the vision protector with the protective window in an open position, and a welding-handle-mounted actuator coupled to the vision protector by a rope wire.

DETAILED DESCRIPTION OF THE INVENTION

Figure 2:
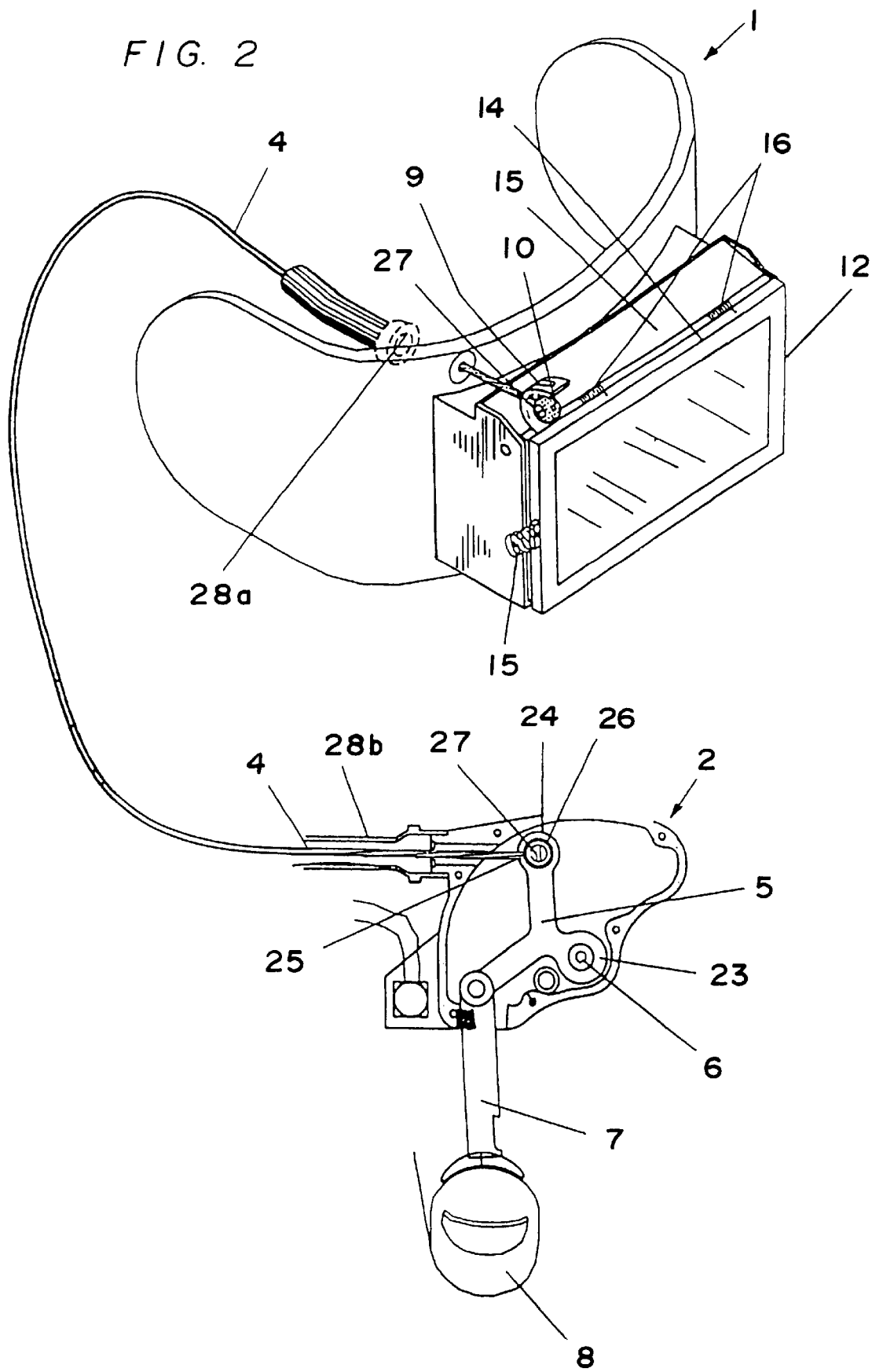
FIG. 2 is a perspective and schematic view of the vision protector with protective window in a closed position, together with the welding-handle-mounted actuator having a distended plug.

FIG. 1 shows a welder's vision protector 1 having a housing unit connected (preferably pivotably connected) to a window frame 12 (sometimes referred to as "filter-holder window.") Vision protector 1 is connected to a window actuator 2 through a sheath 3 and a wire rope 4. In operation, when pressing actuator plug 7 with finger 8, lever 5 pivots on finger lever fulcrum 6 and actuates wire rope 4. A first end of rope 4 is coupled to a first anchor 10 (sometimes referred to as a "screwed-sphere," or "wire rope-press head," or "plug-press head") through a curvilinear (preferably spherical) flange 9 mounted on an edge of window frame 12. The first anchor is captured by and in rotatable opposition to the slotted flange. Preferably, the first anchor is also spherical in shape.

The filter-holder may be made from a plastic thermostable or thermoformable material or fiberglass, and may have a metal coating. Flange 9 has an inside surface sized to capture first anchor 10 of wire rope 4 and a substantially vertical first slot 13 having a width so as to receive wire rope 4 with minimal to no friction. Flange 9 is supported on and rotates about pivot point 11. When flange 9 is acted upon by first anchor 10 of wire rope 4, window frame 12 is raised (i.e., it opens). First slot 13 allows rotation of flange 9 during the opening and closing of window frame 12, without altering the orientation of wire rope 4 between sheath 3 and anchor 10, which is generally a linear and horizontal path. Thus, flange 9, together with slot 13, enables the segment of wire rope 4 which extends from first coupler 28a to flange 9 to remain in a path that is essentially coaxial with the longitudinal axis of the portion of sheath 3 proximate first coupler 28a.

Between window arm 15a and a top front edge 14a of window frame 12, and between lateral spring ends 14 and 15 of window frame 12, are a plurality of springs 16, including top compression-type springs and at least one lateral tension springs. Each of springs 16 are gauged and designed to close window frame 12 when actuator plug 7 is released. Window frame 12 can be locked open by pressing plug 7 with finger 8 and, at the same time, by shifting plug 7 from line 19 in order to align whetstone cavity 17 of plug 7 with whetstone wedge 18. Window frame 12 is unlocked by again pressing plug 7 in and shifting it back towards line 19, thereby dislodging wedge 18 from cavity 17. Thereafter, as finger 8 is withdrawn from plug 7, window frame 12 is again closed due to springs 16.

Window actuator 2 may also include a mechanism to energize or to de-energize a welder's cutting implement by means of a wireless switch 20 or battery, located in the handle of the welding tool, to affect a signal to a shut-off mechanism in the welding or cutting mechanism. The wireless switch sends a signal to the cutting equipment which interrupts the flow of energy to the cutter. For both the wire-rope-tethered and wireless actuators, energy flow is interrupted whenever window frame 12 is in an open position due to the position of sensors 21 and 22, as a function of plug 7. Plug 7 is fitted with a safety sensor. The sensor is in communication with a mirror located in the finger plug. Thus, energy is supplied to a welding tool as a function of movement of finger plug 7 and of sensors 21 and 22. Similarly, when finger plug 7 is distended and window frame 12 is closed by the springs, energy flow may resume.

FIG. 2 shows a vision protector 1 in a closed position, with plug 7 distended. As finger 8 is withdrawn from plug 7, springs 16 are gauged to draw window frame 12 into a closed position. Actuator 2 is provided with an internal lever 5, preferably V-shaped or Y-shaped. Lever 5 has a first end connected to plug 7 at an end of plug 7 opposite finger 8. Between the first end and a second end of lever 5 is finger lever fulcrum 6, and central hole 23 formed through fulcrum 6, about which lever 5 pivots.

The second end of lever 5 has formed therethrough a socket 24 which receives second anchor 26 with minimal friction. Second anchor 26 is curvilinear in shape, preferably cylindrical or spherical, and is rotatably receivable in socket 24. Preferably anchor 26 is connected to the wire rope using a grub screw 27. Grub screw 27 may rotate independently of second anchor 26. A grub screw 27 may be similarly disposed in first anchor 10.

Socket 24 joins and otherwise communicates with a substantially vertical second slot 25 formed through the second end of lever 5. Second slot 25 serves a function similar to first slot 13 of flange 9. More specifically, second slot 25 enables wire rope 4, even while lever 5 is rotated about finger lever fulcrum 6, to maintain a substantially stable and level disposition. Preferably, rope 4 can maintain an essentially coaxial extension with the longitudinal axis of sheath 3, proximate coupler 28(b). Second slot 25 also serves to minimize friction upon, or disorientation of, wire rope 4.

The spherical shape of first anchor 10 and second anchor 26 permits the anchors to rotate relative to flange 9 and socket 24, respectively. The use of the grub screw 27 and the rotatability of the flange with respect to the frame, enables the wire rope to maintain its essentially horizontal disposition. This enables relative ease of movement with minimal twisting of wire rope 4 relative to the vision protector 1, or relative to the handle of the cutting equipment or actuator 2. It also keeps the vision protector from throttling or failing due to twisting of wire rope 4, or the window actuator 2 from having its operation compromised. Each of the ends of sheath 3 maintain a coupler, together comprising a coupler system (28a and 28b). Couplers 28a and 28b enable wire 4 to remain firmly joined to vision protector 1 and to actuator 2, respectively. The couplers also make it easy for wire 4 to rotate on its axis without any detaching, throttling or breaking.

Figure 3:
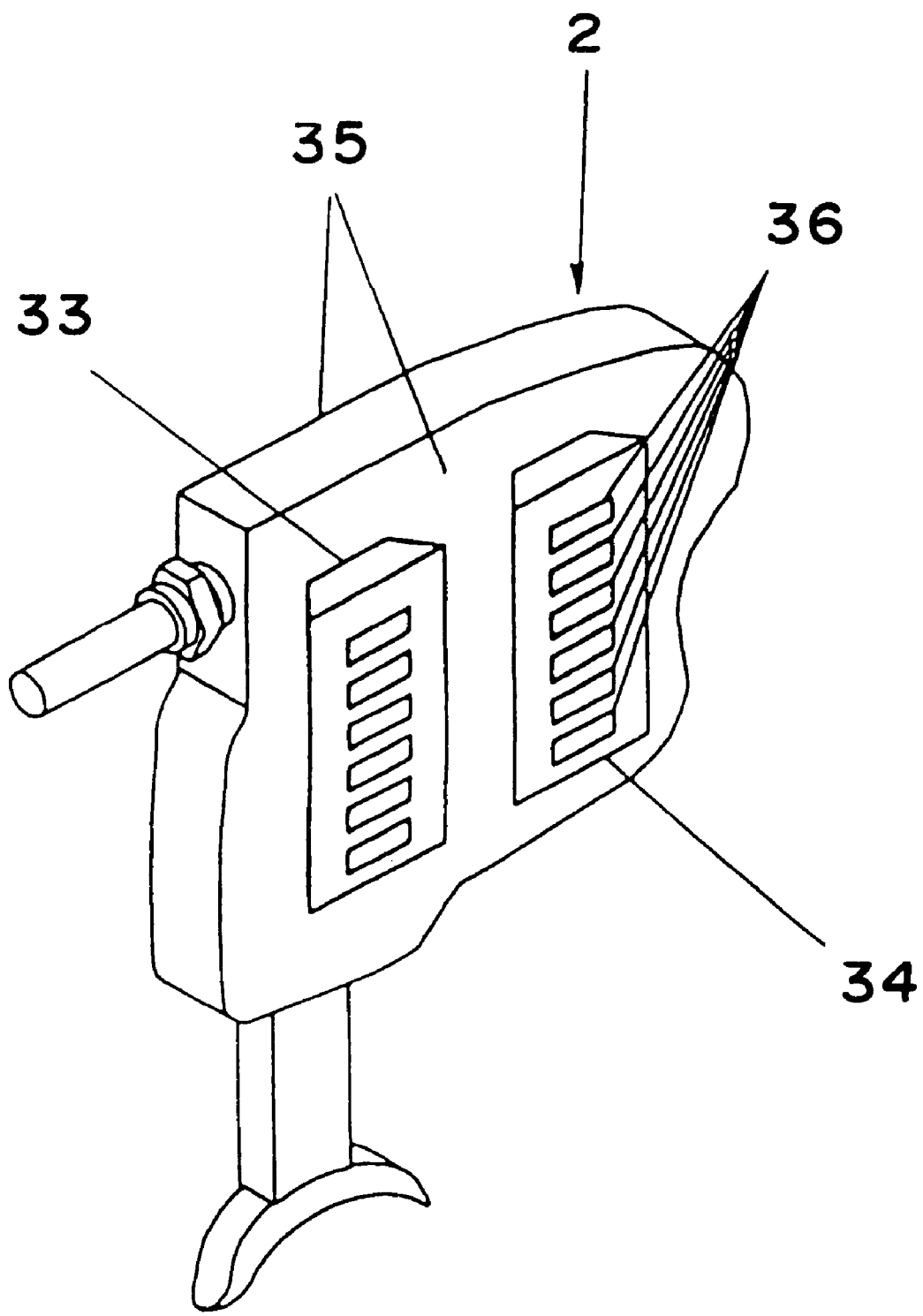
FIG. 3 shows a perspective view of a modular welding-handle-mounted L-shaped connector base that can be slidably coupled to a window actuator using complementary tapered bars, and without using holding screws.

Referring to FIG. 3, window actuator 2 maintains side lids 35 upon which are mounted two trapezoidal or tapered bars 33 and 34 for anchoring the actuator to the welding implement. Bars 33 and 34 maintain a plurality of cavities 36 into each of which a preferably rectangular adjustment pin 41 of a base extends. The tapered bars anchor actuator 2 to the electrode-holder pliers or cutting handle, so as to make it suitable for use by right-handed and left-handed operators alike.

Figure 4:
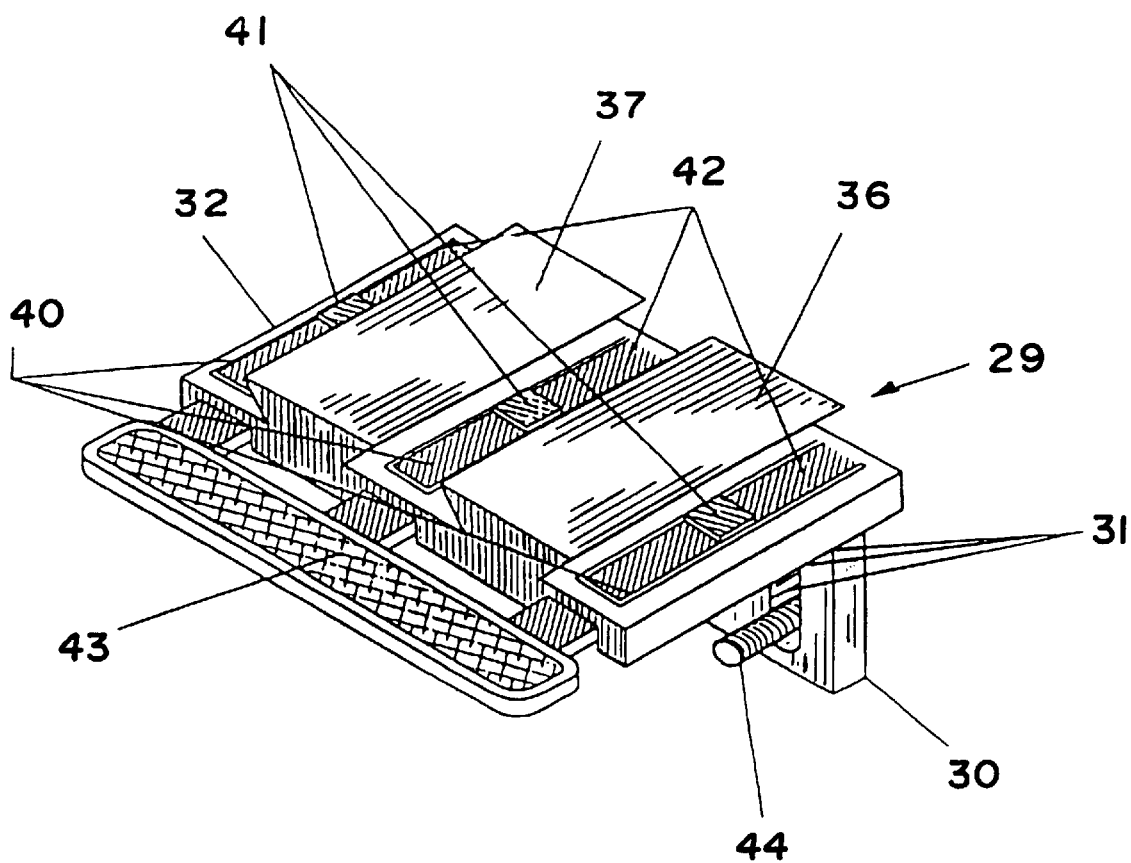
FIG. 4 shows a perspective view of a welding-handle-mounted L-shaped connector base that can be slidably coupled to a window actuator using complementary tapered bars, and without using holding screws.

FIG. 4 shows an L-shaped connector base 29 having a wing 30 with parallel slots 31. Base 29 is coupled to both actuator 2 as well as to a cutting handle of a welding mechanism. Preferably, at least one screw 44 extends through one of the slots 31 so as to fasten base 29 to the cutting handle. Preferably at least two tapered bars, 37 and 38, are mounted upon wing 32 in order to couple connector base 29 to actuator 2. Tapered bars 37 and 38 of base 29 preferably interlock with tapered bars 33 and 34 of actuator 2. Base 29 includes at least three rectangular bars 40, each of which runs lengthwise along the side edges of bars 37 and 38. Each of bars 40 is provided with a rectangular adjustment pin 41. Pin 41 is receivable in the cavities 36 so as to afford any necessary adjustments between base 29 and the actuator. Bars 40 attach to the base at ends 42. Opposite from ends 42, bars 40 are coupled to pulse button 43. When pushed, pulse button 43 depresses pins 41 and thereby disengages pins 41 from cavities 36. In this way, several welders can use the same equipment with the appropriate protectors, and adjust them at their discretion and convenience.

Figure 5:
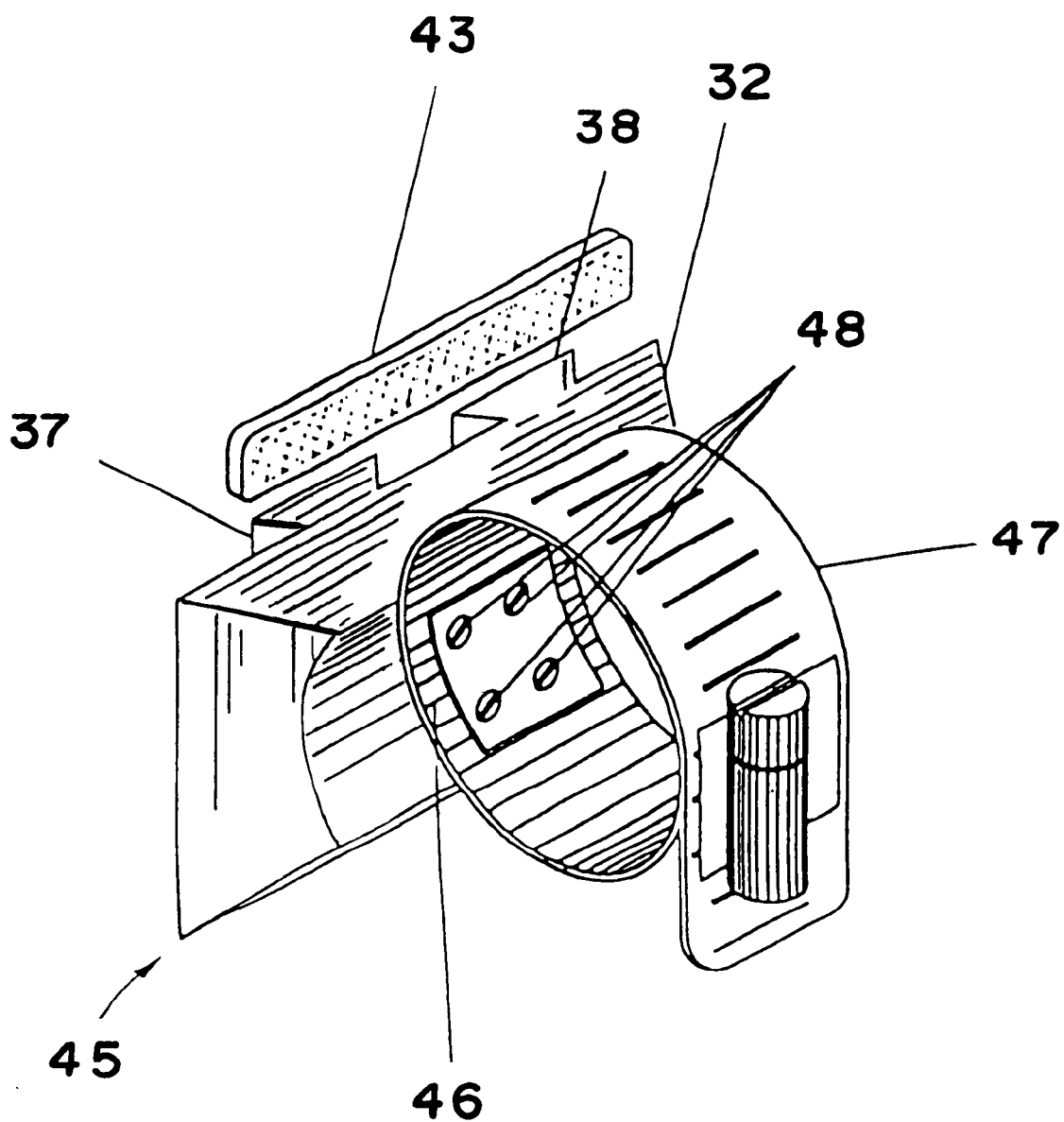
FIG. 5 shows a worm-clamp connector base designed to mount the window actuator to a cutting or welding handle without using a set screw.

FIG. 5 shows an alternate, preferably rectangular connector base 45, utilizing a worm clamp. Base 45 is coupled to window actuator 2 using the tapered bars 37 and 38, rectangular bars 40, and pins 41 shown in FIG. 4. However, in this case, the preferred means for attaching rectangular base 45 to a cutting handle is a substantially ring-shaped cylinder, such as a conventional worm clamp 47. Worm clamp 47 is coupled to base 45, preferably a plurality of screws. In essence, rectangular base 45 is designed to anchor actuator 2 to a handle of cutting equipment without the need for a setscrew.

Figure 6:
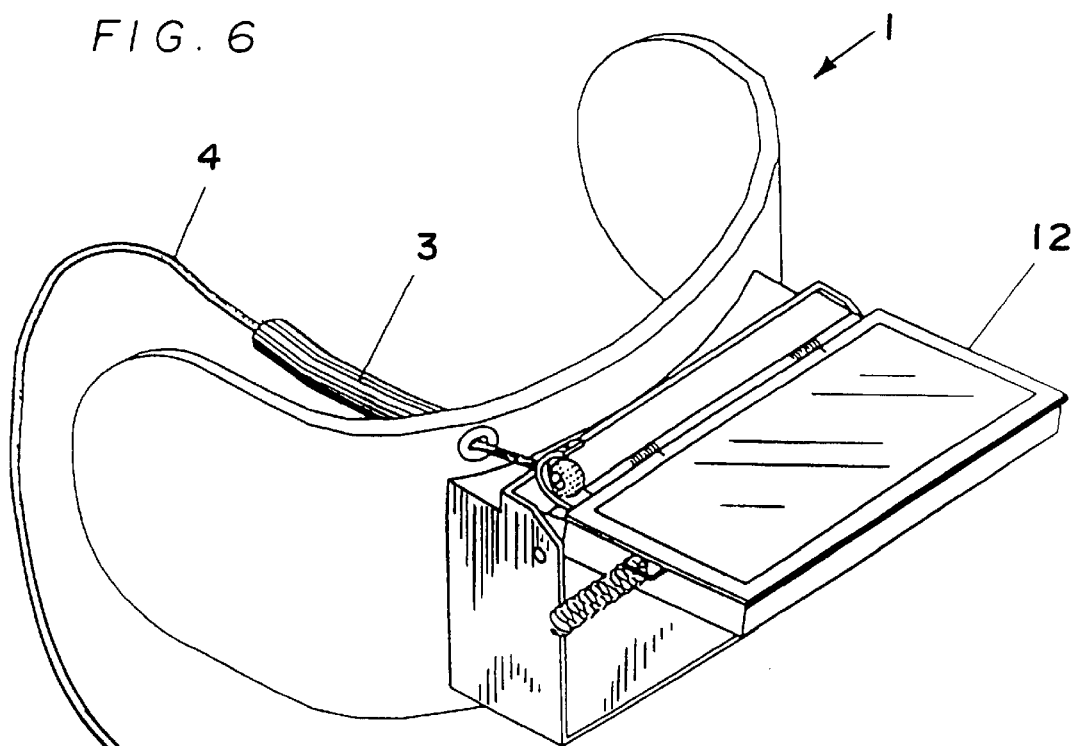
FIG. 6 shows a perspective and schematic view of a vision protector having a foot pedal actuated window
Figure 6:
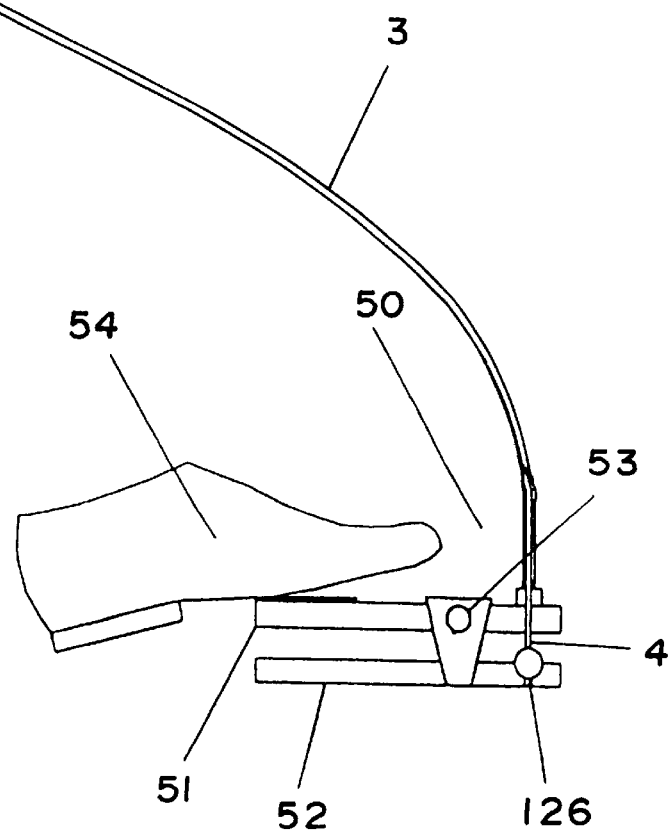

Now referring to FIG. 6, which shows vision protector 1 with window frame 12 in an open position, as in FIG. 1. In FIG. 6, the actuator is foot-driven by means of a foot lever actuator 50. Applying downward pressure through foot 54 onto a front segment of lever 51 (i.e., towards base 52) causes rotation of lever 51 about foot lever fulcrum 53. This results in retraction of wire rope 4 inside sheath 3. This is due, in part, to the fact that wire rope 4 is coupled to base 52 through third anchor 126 of wire rope 4. Head 126 is preferably spherical in shape.

Figure 7:
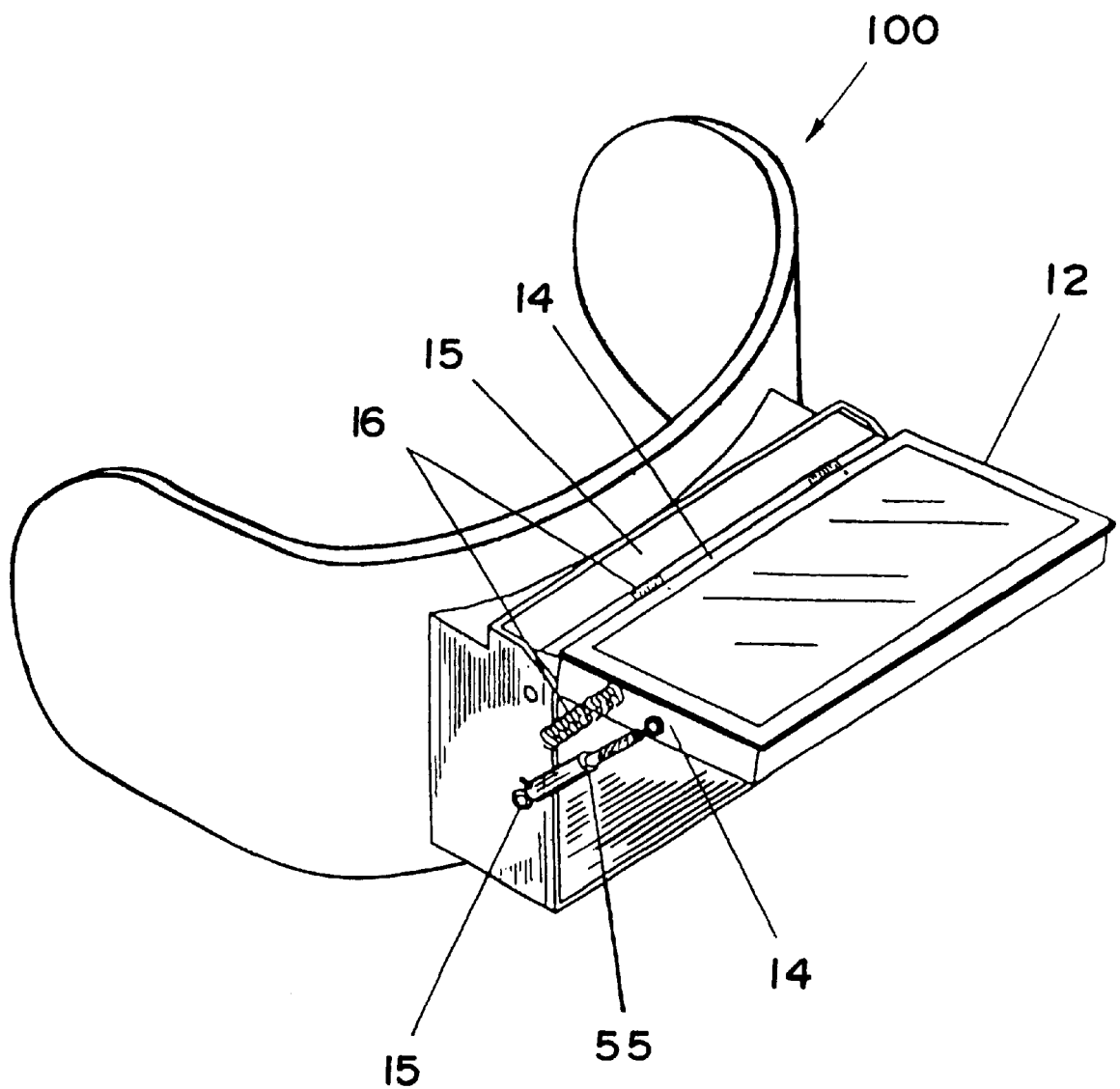
FIG. 7 shows a perspective view of a vision protector with the window openable by means of an air or oil-driven dual-acting plug.

In reference to FIG. 7, window frame 12 of vision protector 100 may be varied by having a dual-acting plug 55 spanning between points 14 and 15. Dual-acting plug 55 is fed by a hose connected to actuator 2. When loaded with oil or air pressure, plug 55 is extensible so as to open window frame 12 as a function of actuating devices such as those in FIG. 8. When plug 7 is released, again however, window frame 12 may automatically close due to springs 16.

Figure 8:
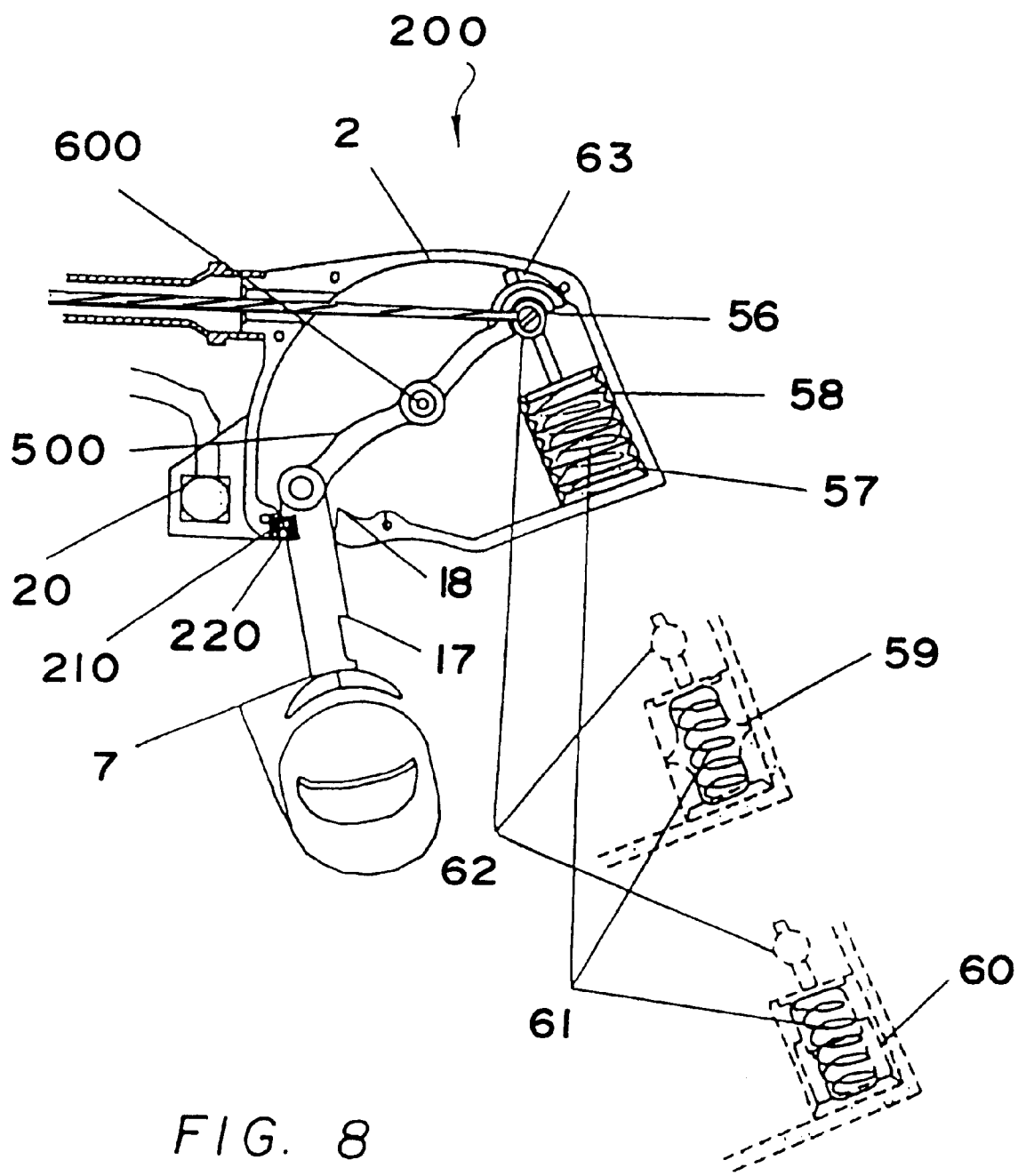
FIG. 8 shows a side and schematic view of a finger-operable, pneumatic or hydraulic actuated vision protector of bellow, diaphragm, or plug-type.

FIG. 8 shows window actuator 200 which manually triggers the vision protector 100 shown in FIG. 7. Again, window frame 12 is triggered or opened by air or oil pressure. Actuator 200 is outfitted with lever 500, which pivots about axis 600. As plug 7 is pressed inward, the space between the points 56 and 57 closes, thus contracting air bellow 58 or diaphragm 59, or plug 60. This contraction creates units of air or oil pressure (air for Bellow 58, air or oil for diaphragm 59, and air or oil for plug 60) which acts upon plug 55 of FIG. 7 to open window frame 12. As finger 8 is released, spring 61 will decompress, as will the pressurizing mechanisms detailed above. Pitchfork 63, at the end of the lever 500, is supported by spherical member 62. As in FIG. 1, whetstone cavity 17 may receive wedge 18 to lock open window frame 12 without requiring further manual pressure by finger 8. Actuator 200 may also include the side lids of actuator 2 in FIG. 3 including tapered bars 37–38 for insertion into either the base 29 of FIG. 4 or the base 45 of FIG. 5 as required by the operator; it may also have the same microswitch 20, and opposing sensors 210 and 220.

Figure 9:
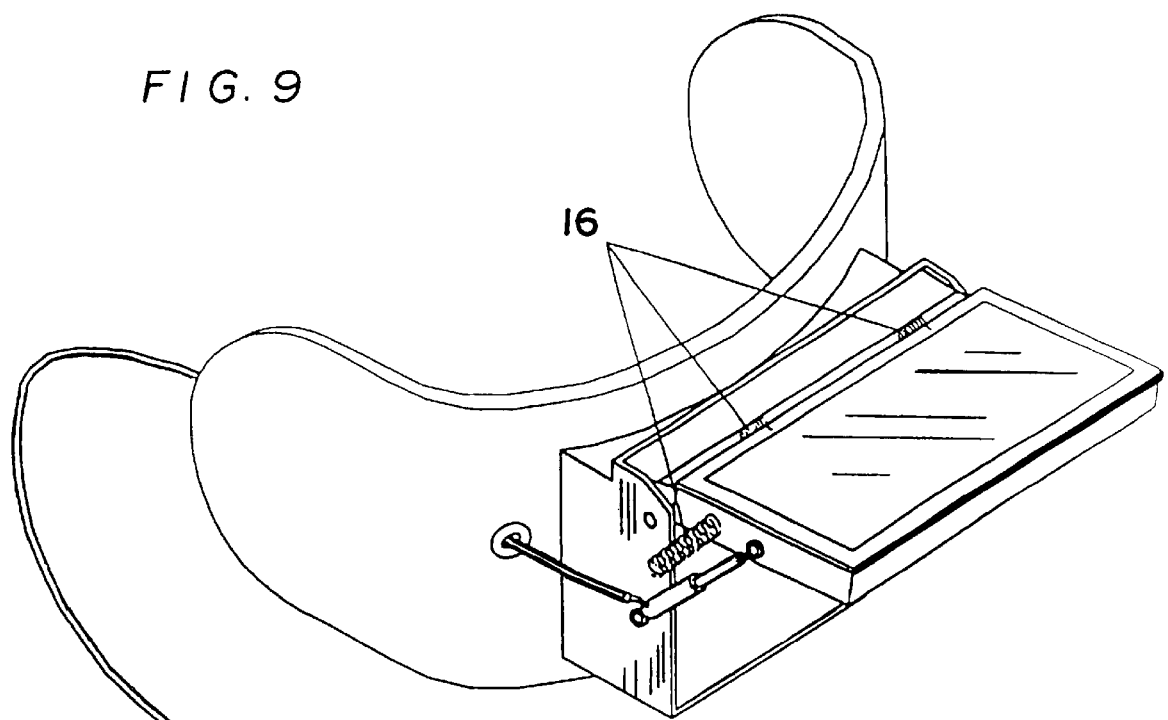
FIG. 9 shows a perspective and schematic view of a pneumatic or hydraulic actuated vision protector operable by a foot.
Figure 9:
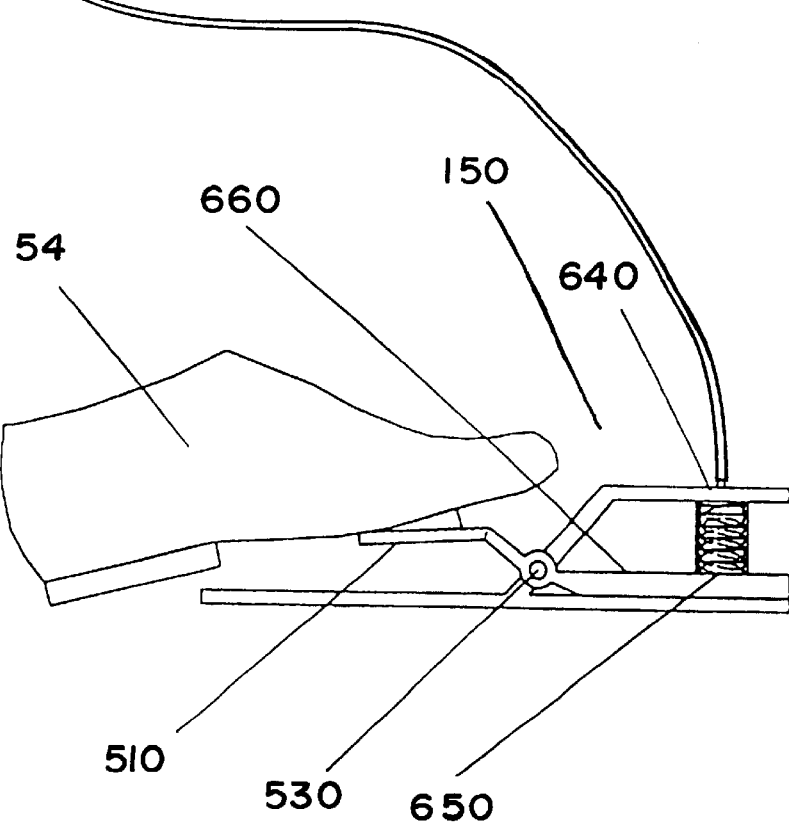

FIG. 9 shows a pedal device 150 to be operated by foot 54, which triggers a pneumatic or hydraulic vision protector 100, as shown in FIG. 7. The design also allows for the couple pressure units such as those in FIG. 8. Such devices produce air or oil pressure when contracting the space between points 640 and 650 due to the pressing of pedal 510. This makes pivot lever 660 pivot about point 530. The manner of closing window frame 12 is the same as in FIG. 2—that is, through springs 16 immediately after the pressure is released by foot 54.

Figure 10:
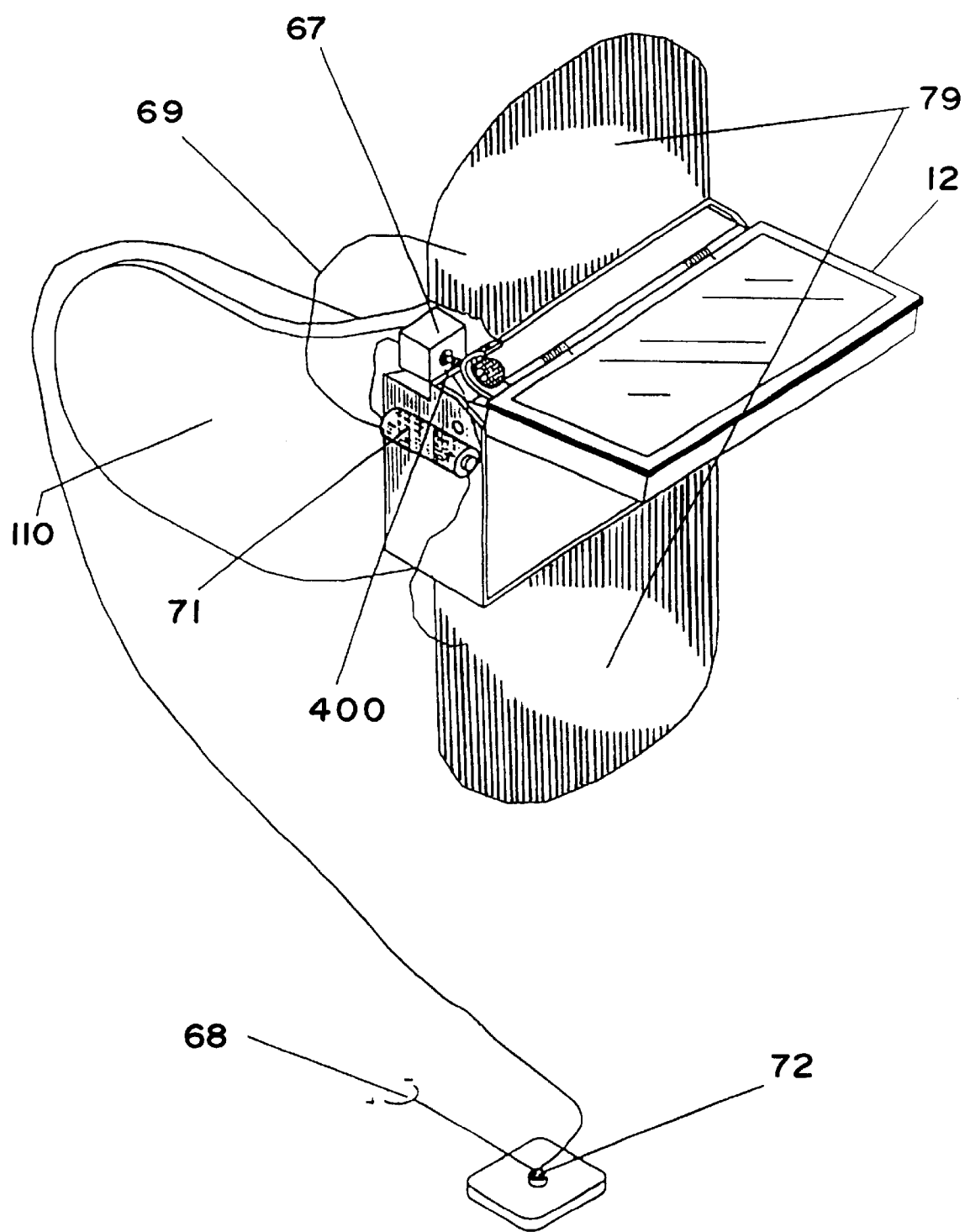
FIG. 10 shows a perspective and schematic view of a solar or electric-powered, push-button-actuated vision protector with the protective window in an open position. An electromagnetic work element is also shown. The automatic push button is located on the welding handle.

FIG. 10 shows a vision protector 110 similar to that of FIG. 1, but different in the sense that here, window frame 12 is lifted by electromagnet 67 which tugs at wire rope link 400. Link 400 is connected through flange 9 to a wire rope anchor, similar to the first anchor shown in FIGS. 1, 2 and 6. Electromagnet 67 is powered by means of electric power 68 or by solar power 69 received through solar panels 79 located about window frame 12. The solar energy is accumulated and store in batteries 71. Button 72, located on the welding handle, may communicate wirelessly with electromagnet 67. Button 72 activates and deactivates electromagnet 67 to open and shut window from 12. Electromagnet 67 opens window from 12 in otherwise a similar manner to that described in FIG. 1 (first anchor 10 acts upon flange 9 to lift up window frame 12, etc). Again, window frame 12 shuts, as in FIG. 2, by means of springs 16 about window frame 12.

What is claimed is:

1. An eye protection device, comprising:
    a window frame coupled to a housing unit;
    a slotted flange pivotally coupled to the window frame;
    a wire rope anchor captured by and in rotatable opposition to the slotted flange;
    a wire rope extending through the slotted flange and coupled to the wire rope anchor; and
    a window frame actuator coupled to the wire rope.

2. A safety apparatus for welders, comprising:
    a window frame coupled to a housing unit;
    a curvilinear slotted flange pivotally coupled to the window frame;
    a first anchor rotatably coupled to a wire rope, the first anchor being captured by, and in rotatable association with, the slotted flange;
    the wire rope coupled to the wire rope anchor through the slotted flange; and
    a window frame actuator coupled to the wire rope and mounted to a base, the base affixed to a welding tool handle.

3. The apparatus according to claim 2, further comprising interlocking tapered bars slidingly connecting the window frame actuator to the base.

4. The apparatus according to claim 3, wherein the window frame actuator is adjustably mounted to the base.

5. The apparatus according to claim 4, further comprising an adjustment pin disposed between each of said tapered bars.

6. The apparatus according to claim 5, wherein the number of tapered bars is at least two on each of the actuator and the base.

7. A safety apparatus for welders, comprising:
    a window frame coupled to a housing unit;
    a slotted flange pivotingly coupled to the window frame;
    a first anchor rotatably coupled to a first end of a wire rope, the first anchor captured by, and in rotatable association with, the slotted flange;
    a wire rope actuator coupled to a second end of the wire rope, and the actuator also coupled to a welding tool handle, said actuator further comprising; and
    a window frame actuator coupled to the second end of the wire rope, and to the welding tool handle, said window frame actuator further comprising:
        a second anchor coupled to the wire rope;
        a lever having a first end connected to a finger plug; and
        a slotted socket formed within a second end of the lever for guiding the rope wire, and for rotatably receiving the second anchor.

8. The apparatus according to claim 7, wherein the slotted socket has a spherical interior surface.

9. The apparatus according to claim 7, wherein the finger plug is fitted with a safety sensor which controls the energy to a welding tool.

10. The apparatus according to claim 7, further comprising a worm screw connected to the wire rope, the worm screw slidingly rotatable relative to the second anchor.

11. The device or apparatus according to claims 1, 2 or 7, wherein the wire rope anchor or first anchor is spherical in shape.

12. The device or apparatus according to claims 1, 2 or 7, wherein the window frame actuator is finger or foot operable.

13. The device or apparatus according to claims 1, 2 or 7, further comprising a spring urging into a closed position and coupled to the window frame.

14. The device or apparatus according to claims 1, 2 or 7, wherein the window frame actuator comprises a finger-operated pneumatic device coupled to the wire rope.

15. The device or apparatus according to claims 1, 2 or 7, wherein the window frame actuator comprises a finger-operated hydraulic device coupled to the wire rope.

16. The device or apparatus according to claims 1, 2 or 7, wherein the window frame actuator comprises an electromagnet in proximity to the wire rope anchor or first anchor.

17. The device or apparatus according to claim 16, wherein the window frame actuator further comprises a button-operable wireless device which transmits a signal to the electromagnet.

18. The device or apparatus according to claim 16, wherein the electromagnet is solar powered.

19. The device or apparatus according to claim 16, wherein the electromagnet is electric powered.

* * * * *

UNITED STATES PATENT AND TRADEMARK OFFICE
CERTIFICATE OF CORRECTION

PATENT NO. : 6,507,954 B1
DATED : January 21, 2003
INVENTOR(S) : John Alejandro Sanchez Talero It is certified that error appears in the above-identified patent and that said Letters Patent is hereby corrected as shown below:

<u>Title page,</u>
Item [76], the inventor's name should read -- John Alejandro Sanchez Talero --

Signed and Sealed this

Twentieth Day of May, 2003

JAMES E. ROGAN
*Director of the United States Patent and Trademark Office*